United States Patent
Batchelor et al.

(10) Patent No.: US 12,257,690 B2
(45) Date of Patent: Mar. 25, 2025

(54) BIAS DEVICE FOR BIASING A GRIPPING DEVICE BY BIASING WORKING ARMS APART

(71) Applicant: GYRUS ACMI, INC., Westborough, MA (US)

(72) Inventors: Kester Julian Batchelor, Mound, MN (US); Riyad Moe, Madison, WI (US)

(73) Assignee: Gyrus ACMI, Inc., Westborough, MA (US)

( * ) Notice: Subject to any disclaimer, the term of this patent is extended or adjusted under 35 U.S.C. 154(b) by 355 days.

(21) Appl. No.: 17/811,509

(22) Filed: Jul. 8, 2022

(65) Prior Publication Data

US 2023/0001564 A1 Jan. 5, 2023

Related U.S. Application Data

(63) Continuation of application No. 15/801,379, filed on Nov. 2, 2017, now Pat. No. 11,383,373.

(51) Int. Cl.
*B25B 7/08* (2006.01)
*A61B 17/28* (2006.01)
(Continued)

(52) U.S. Cl.
CPC ............... *B25G 1/102* (2013.01); *B25B 7/06* (2013.01); *B25B 7/08* (2013.01); *B25B 7/18* (2013.01);
(Continued)

(58) Field of Classification Search
CPC ......... A61B 17/28; A61B 17/29; A61B 17/30; A61B 17/50; A61B 2017/505; A61B 2017/2946; A61B 18/1442; A61B 2018/1462; A61F 2/1664; A61F 2/007; A61F 2/00781; A61C 3/10; A45D 26/0066; A45D 29/18; B25B 9/00; B25B 9/02; B25B 7/123; B25B 7/14; B25B 7/16; B25B 7/18; B25B 7/06; B25B 7/08; B25B 13/12;
(Continued)

(56) References Cited

U.S. PATENT DOCUMENTS 1,198,958 A 9/1916 Risley
2,042,985 A 6/1936 Gardella
(Continued)

FOREIGN PATENT DOCUMENTS

EP 0392548 A1 10/1990
EP 1530952 A1 5/2005
(Continued)

OTHER PUBLICATIONS

"U.S. Appl. No. 15/801,379, Final Office Action mailed Apr. 6, 2021", 9 pgs.
(Continued)

*Primary Examiner* — Diane D Yabut
(74) *Attorney, Agent, or Firm* — Schwegman Lundberg & Woessner, P.A.

(57) ABSTRACT

A device comprising: (a) a first working arm; (b) a shuttle located on the first working arm, and (c) a bias device; wherein the bias device biases the first working arm when the shuttle is in a first position, and wherein the bias device is free of biasing the first working arm when the shuttle is in a second position.

19 Claims, 6 Drawing Sheets

(51) Int. Cl.
  *B25B 7/06* (2006.01)
  *B25B 7/18* (2006.01)
  *B25B 9/02* (2006.01)
  *B25G 1/10* (2006.01)
  *B26B 13/16* (2006.01)
  *F16F 1/368* (2006.01)

(52) U.S. Cl.
  CPC ............... *B25B 9/02* (2013.01); *B26B 13/16* (2013.01); *A61B 17/28* (2013.01); *A61B 17/2841* (2013.01); *B25G 1/10* (2013.01); *F16F 1/368* (2013.01)

(58) Field of Classification Search
  CPC .......... B25B 13/14; B25B 13/16; B25G 1/10; B25G 1/102; F16F 1/368; G04D 1/021
  See application file for complete search history.

(56) References Cited

U.S. PATENT DOCUMENTS

| | | |
|---|---|---|
| 2,214,984 A | 9/1940 | Henry |
| 2,381,084 A | 8/1945 | Slad |
| 2,575,652 A | 11/1951 | Bovee |
| 2,894,424 A | 7/1959 | Vaughan, Jr. |
| 3,399,583 A | 9/1968 | Lance |
| 3,417,752 A | 12/1968 | Butler |
| 3,465,621 A | 9/1969 | Ladd |
| 3,576,072 A | 4/1971 | Foster |
| 3,643,663 A | 2/1972 | Sutter |
| 3,685,518 A | 8/1972 | Beuerle et al. |
| 3,699,632 A | 10/1972 | Anhalt |
| 3,818,784 A | 6/1974 | McClure |
| 3,906,957 A | 9/1975 | Weston |
| 3,913,586 A | 10/1975 | Baumgarten |
| 4,023,450 A | 5/1977 | Ygfors |
| 4,041,952 A | 8/1977 | Morrison, Jr. et al. |
| 4,154,226 A | 5/1979 | Hennig et al. |
| 4,171,700 A | 10/1979 | Farin |
| 4,202,337 A | 5/1980 | Clark et al. |
| 4,318,313 A | 3/1982 | Tartaglia |
| 4,375,218 A | 3/1983 | Digeronimo |
| 4,387,610 A | 6/1983 | Sergeant |
| 4,407,069 A | 10/1983 | Conners |
| 4,418,692 A | 12/1983 | Guay |
| 4,443,935 A | 4/1984 | Zamba et al. |
| 4,452,106 A * | 6/1984 | Tartaglia ............ A61B 17/3201 294/902 |
| 4,462,404 A * | 7/1984 | Schwarz ............ A61B 17/2812 81/313 |
| 4,463,759 A | 8/1984 | Garito et al. |
| 4,492,231 A | 1/1985 | Auth |
| 4,492,832 A | 1/1985 | Taylor |
| 4,494,543 A | 1/1985 | Hart |
| 4,504,707 A | 3/1985 | Ochiai |
| 4,524,648 A | 6/1985 | Chung |
| 4,552,143 A | 11/1985 | Lottick |
| 4,655,215 A | 4/1987 | Pike |
| 4,669,470 A | 6/1987 | Brandfield |
| 4,686,980 A | 8/1987 | Williams et al. |
| 4,713,885 A | 12/1987 | Keklak et al. |
| 4,757,612 A | 7/1988 | Peyrot |
| 4,784,136 A | 11/1988 | Klein |
| 4,839,947 A | 6/1989 | Cohen et al. |
| 4,860,745 A | 8/1989 | Farin et al. |
| 4,896,661 A | 1/1990 | Bogert |
| 4,935,027 A | 6/1990 | Yoon |
| 5,021,616 A | 6/1991 | Hardt |
| 5,035,695 A | 7/1991 | Weber, Jr. et al. |
| 5,071,426 A | 12/1991 | Dolgin et al. |
| 5,104,397 A | 4/1992 | Vasconcelos et al. |
| 5,108,392 A | 4/1992 | Spingler |
| 5,147,378 A | 9/1992 | Markham |
| 5,176,702 A | 1/1993 | Bales et al. |
| 5,190,541 A | 3/1993 | Abele et al. |
| 5,196,009 A | 3/1993 | Kirwan, Jr. |
| 5,207,691 A | 5/1993 | Nardella |
| 5,207,696 A | 5/1993 | Matwijcow |
| 5,208,983 A | 5/1993 | Masse |
| 5,226,904 A | 7/1993 | Gentelia et al. |
| 5,250,056 A | 10/1993 | Hasson |
| 5,281,216 A | 1/1994 | Klicek |
| 5,290,286 A | 3/1994 | Parins |
| 5,293,878 A | 3/1994 | Bales et al. |
| 5,318,589 A | 6/1994 | Lichtman |
| 5,342,359 A | 8/1994 | Rydell |
| 5,370,659 A | 12/1994 | Sakashita |
| 5,403,312 A | 4/1995 | Yates et al. |
| 5,413,575 A | 5/1995 | Haenggi |
| 5,423,814 A | 6/1995 | Zhu et al. |
| 5,425,743 A | 6/1995 | Nicholas |
| 5,440,813 A | 8/1995 | Roskam |
| 5,441,498 A | 8/1995 | Perkins |
| 5,443,463 A | 8/1995 | Stern et al. |
| 5,456,695 A | 10/1995 | Herve Dallemagne |
| 5,458,598 A | 10/1995 | Feinberg et al. |
| 5,472,442 A | 12/1995 | Klicek |
| 5,483,952 A | 1/1996 | Aranyi |
| 5,484,435 A | 1/1996 | Fleenor et al. |
| 5,499,998 A | 3/1996 | Meade |
| 5,531,744 A | 7/1996 | Nardella et al. |
| 5,540,685 A | 7/1996 | Parins et al. |
| 5,562,503 A | 10/1996 | Ellman et al. |
| 5,573,424 A | 11/1996 | Poppe |
| 5,619,892 A | 4/1997 | Eggert |
| 5,626,577 A | 5/1997 | Harris |
| 5,658,281 A | 8/1997 | Heard |
| D386,054 S | 11/1997 | Litton |
| 5,702,390 A | 12/1997 | Austin et al. |
| 5,709,680 A | 1/1998 | Yates et al. |
| 5,735,849 A | 4/1998 | Baden et al. |
| 5,779,701 A | 7/1998 | Mcbrayer et al. |
| 5,810,805 A | 9/1998 | Sutcu et al. |
| 5,827,281 A | 10/1998 | Levin |
| 5,884,954 A | 3/1999 | Trozera |
| 5,891,140 A | 4/1999 | Ginn et al. |
| 5,902,301 A | 5/1999 | Olig |
| 5,922,001 A | 7/1999 | Yoon |
| 5,951,545 A | 9/1999 | Schilling et al. |
| 6,024,741 A | 2/2000 | Williamson, IV et al. |
| 6,030,384 A | 2/2000 | Nezhat |
| 6,039,734 A | 3/2000 | Goble |
| 6,050,996 A | 4/2000 | Schmaltz et al. |
| 6,053,908 A | 4/2000 | Crainich et al. |
| 6,074,386 A | 6/2000 | Goble et al. |
| 6,102,909 A | 8/2000 | Chen et al. |
| 6,110,171 A | 8/2000 | Rydell |
| 6,113,596 A | 9/2000 | Hooven et al. |
| 6,117,158 A | 9/2000 | Measamer et al. |
| 6,117,169 A | 9/2000 | Moe |
| 6,152,923 A | 11/2000 | Ryan |
| 6,190,386 B1 | 2/2001 | Rydell |
| 6,270,497 B1 | 8/2001 | Sekino et al. |
| 6,273,887 B1 | 8/2001 | Yamauchi et al. |
| 6,325,795 B1 | 12/2001 | Lindemann et al. |
| 6,355,032 B1 | 3/2002 | Hovda et al. |
| 6,358,268 B1 | 3/2002 | Hunt et al. |
| 6,402,747 B1 | 6/2002 | Lindemann et al. |
| 6,428,538 B1 | 8/2002 | Blewett et al. |
| 6,458,128 B1 | 10/2002 | Schulze |
| 6,464,704 B2 | 10/2002 | Schmaltz et al. |
| 6,486,419 B2 | 11/2002 | Horiguchi et al. |
| 6,494,886 B1 | 12/2002 | Wilk et al. |
| 6,514,252 B2 | 2/2003 | Nezhat et al. |
| 6,551,313 B1 | 4/2003 | Levin |
| 6,585,735 B1 | 7/2003 | Frazier et al. |
| 6,619,038 B2 | 9/2003 | Takada et al. |
| 6,623,499 B1 | 9/2003 | Andreini et al. |
| 6,641,595 B1 | 11/2003 | Moran et al. |
| 6,652,514 B2 | 11/2003 | Ellman et al. |
| 6,679,882 B1 | 1/2004 | Kornerup |
| 6,695,840 B2 | 2/2004 | Schulze |
| 6,726,686 B2 | 4/2004 | Buysse et al. |
| 6,749,610 B2 | 6/2004 | Kirwan, Jr. et al. |

(56) References Cited

U.S. PATENT DOCUMENTS

| | | | |
|---|---|---|---|
| 6,752,767 B2 | 6/2004 | Turovskiy et al. |
| 6,773,434 B2 | 8/2004 | Ciarrocca |
| 6,808,525 B2 | 10/2004 | Latterell et al. |
| 6,827,717 B2 | 12/2004 | Brommersma et al. |
| 6,860,882 B2 | 3/2005 | Battles et al. |
| 6,926,716 B2 | 8/2005 | Baker et al. |
| 6,942,662 B2 | 9/2005 | Goble et al. |
| 6,988,814 B1 * | 1/2006 | Correa .................... B25B 9/02 362/184 |
| 7,083,613 B2 | 8/2006 | Treat |
| 7,094,231 B1 | 8/2006 | Ellman et al. |
| 7,108,694 B2 | 9/2006 | Miura et al. |
| 7,112,199 B2 | 9/2006 | Cosmescu |
| 7,147,637 B2 | 12/2006 | Goble |
| 7,147,638 B2 | 12/2006 | Chapman et al. |
| 7,150,749 B2 | 12/2006 | Dycus et al. |
| 7,156,846 B2 | 1/2007 | Dycus et al. |
| 7,232,440 B2 | 6/2007 | Dumbauld et al. |
| 7,244,257 B2 | 7/2007 | Podhajsky et al. |
| 7,252,667 B2 | 8/2007 | Moses et al. |
| 7,344,536 B1 | 3/2008 | Lunsford et al. |
| 7,367,976 B2 | 5/2008 | Lawes et al. |
| 7,377,902 B2 | 5/2008 | Burbank et al. |
| 7,481,810 B2 | 1/2009 | Dumbauld et al. |
| 7,503,917 B2 | 3/2009 | Sartor et al. |
| 7,604,635 B2 | 10/2009 | Mcclurken et al. |
| 7,625,391 B2 | 12/2009 | Kebel et al. |
| 7,674,261 B2 | 3/2010 | Garito et al. |
| 7,686,827 B2 | 3/2010 | Hushka |
| 7,722,607 B2 | 5/2010 | Dumbauld et al. |
| 7,753,909 B2 | 7/2010 | Chapman et al. |
| 7,758,577 B2 | 7/2010 | Nobis et al. |
| 7,789,878 B2 | 9/2010 | Dumbauld et al. |
| 7,879,035 B2 | 2/2011 | Garrison et al. |
| 7,896,875 B2 | 3/2011 | Heim et al. |
| 7,909,820 B2 | 3/2011 | Lipson et al. |
| 7,922,718 B2 | 4/2011 | Moses et al. |
| 7,931,649 B2 | 4/2011 | Couture et al. |
| 7,931,668 B2 | 4/2011 | Sloat |
| 7,938,469 B2 | 5/2011 | Ait-mani |
| 7,942,872 B2 | 5/2011 | Ein-Gal |
| 7,955,331 B2 | 6/2011 | Truckai et al. |
| 7,998,140 B2 | 8/2011 | Mcclurken et al. |
| 8,062,292 B1 | 11/2011 | Slater |
| 8,100,894 B2 | 1/2012 | Mucko et al. |
| 8,162,940 B2 | 4/2012 | Johnson et al. |
| 8,216,231 B2 | 7/2012 | Behl et al. |
| 8,226,649 B2 | 7/2012 | Falkenstein et al. |
| 8,246,094 B2 | 8/2012 | Long et al. |
| 8,251,989 B1 | 8/2012 | Newton et al. |
| 8,262,655 B2 | 9/2012 | Ghabrial et al. |
| 8,267,935 B2 | 9/2012 | Couture et al. |
| 8,287,534 B2 | 10/2012 | Balog |
| 8,328,170 B2 | 12/2012 | Wasinger |
| 8,485,413 B2 | 7/2013 | Scheib et al. |
| 8,491,626 B2 | 7/2013 | Roy et al. |
| 8,496,603 B2 | 7/2013 | Mamourian |
| 8,555,754 B2 | 10/2013 | Hermann et al. |
| 8,568,411 B2 | 10/2013 | Falkenstein et al. |
| 8,628,529 B2 | 1/2014 | Aldridge et al. |
| 8,632,553 B2 | 1/2014 | Sakamoto et al. |
| 8,702,691 B2 | 4/2014 | Weber et al. |
| 8,702,700 B2 | 4/2014 | Maeda et al. |
| 8,882,756 B2 | 11/2014 | Greeley et al. |
| 8,939,972 B2 | 1/2015 | Twomey |
| 9,023,035 B2 | 5/2015 | Allen, Iv et al. |
| 9,204,879 B2 | 12/2015 | Shelton, Iv |
| 9,320,563 B2 | 4/2016 | Brustad et al. |
| 9,326,810 B2 | 5/2016 | Shilev et al. |
| 9,345,534 B2 | 5/2016 | Artale et al. |
| 9,439,665 B2 | 9/2016 | Marczyk et al. |
| 9,445,863 B2 | 9/2016 | Batchelor et al. |
| 9,452,009 B2 | 9/2016 | Batchelor et al. |
| 9,452,011 B2 | 9/2016 | Batchelor et al. |
| 9,668,805 B2 | 6/2017 | Batchelor et al. |
| 9,707,028 B2 | 7/2017 | Batchelor et al. |
| 9,763,685 B2 | 9/2017 | Batchelor et al. |
| 9,763,730 B2 | 9/2017 | Batchelor et al. |
| 10,667,834 B2 | 6/2020 | Batchelor et al. |
| 11,298,801 B2 | 4/2022 | Batchelor et al. |
| 11,383,373 B2 | 7/2022 | Batchelor et al. |
| 2002/0106609 A1 | 8/2002 | Palermo et al. |
| 2002/0107517 A1 | 8/2002 | Witt et al. |
| 2002/0115997 A1 | 8/2002 | Truckai et al. |
| 2003/0018329 A1 | 1/2003 | Hooven |
| 2003/0050633 A1 | 3/2003 | Ellman et al. |
| 2003/0097126 A1 | 5/2003 | Woloszko et al. |
| 2003/0109876 A1 | 6/2003 | Yamauchi |
| 2003/0114850 A1 | 6/2003 | Mcclurken et al. |
| 2003/0144652 A1 | 7/2003 | Baker et al. |
| 2003/0181904 A1 | 9/2003 | Levine et al. |
| 2004/0030330 A1 | 2/2004 | Brassell et al. |
| 2004/0082946 A1 | 4/2004 | Malis et al. |
| 2004/0097117 A1 | 5/2004 | Gonnering |
| 2004/0097912 A1 | 5/2004 | Gonnering |
| 2005/0065510 A1 | 3/2005 | Carmel et al. |
| 2005/0113824 A1 | 5/2005 | Sartor et al. |
| 2005/0113825 A1 | 5/2005 | Cosmescu |
| 2005/0113827 A1 | 5/2005 | Dumbauld et al. |
| 2005/0159745 A1 | 7/2005 | Truckai et al. |
| 2005/0187512 A1 | 8/2005 | Isola et al. |
| 2005/0216019 A1 | 9/2005 | Eckman |
| 2006/0084973 A1 | 4/2006 | Hushka |
| 2006/0190035 A1 | 8/2006 | Hushka et al. |
| 2006/0217701 A1 | 9/2006 | Young et al. |
| 2007/0049922 A1 | 3/2007 | Rontal |
| 2007/0078458 A1 | 4/2007 | Dumbauld et al. |
| 2007/0093857 A1 | 4/2007 | Rogers et al. |
| 2007/0123855 A1 | 5/2007 | Morley et al. |
| 2007/0129716 A1 | 6/2007 | Daw |
| 2007/0179491 A1 | 8/2007 | Kratoska et al. |
| 2008/0033428 A1 | 2/2008 | Artale et al. |
| 2008/0077129 A1 | 3/2008 | Van et al. |
| 2008/0147092 A1 | 6/2008 | Rogge et al. |
| 2008/0154300 A1 | 6/2008 | Jabbour |
| 2008/0236860 A1 | 10/2008 | Howe |
| 2008/0287948 A1 | 11/2008 | Newton et al. |
| 2009/0062786 A1 | 3/2009 | Garito et al. |
| 2009/0062792 A1 | 3/2009 | Vakharia et al. |
| 2009/0093804 A1 | 4/2009 | Newton |
| 2009/0138003 A1 | 5/2009 | Deville et al. |
| 2009/0138013 A1 | 5/2009 | Thorne et al. |
| 2009/0171147 A1 | 7/2009 | Lee et al. |
| 2009/0192509 A1 | 7/2009 | Curtis et al. |
| 2009/0248002 A1 | 10/2009 | Takashino et al. |
| 2010/0042096 A1 | 2/2010 | Ellman |
| 2010/0087814 A1 | 4/2010 | Desinger et al. |
| 2010/0137854 A1 | 6/2010 | Hosier |
| 2010/0228249 A1 | 9/2010 | Mohr et al. |
| 2011/0045680 A1 | 2/2011 | Beller et al. |
| 2011/0054462 A1 | 3/2011 | Ellman |
| 2011/0077648 A1 | 3/2011 | Lee et al. |
| 2011/0112530 A1 | 5/2011 | Keller |
| 2011/0178515 A1 | 7/2011 | Bloom et al. |
| 2011/0224669 A1 | 9/2011 | Podany |
| 2011/0251613 A1 | 10/2011 | Guerra et al. |
| 2011/0319892 A1 | 12/2011 | Blomeyer |
| 2012/0022530 A1 | 1/2012 | Woodruff et al. |
| 2012/0078292 A1 | 3/2012 | Banju |
| 2012/0095460 A1 | 4/2012 | Rooks et al. |
| 2012/0101501 A1 | 4/2012 | Nishimura et al. |
| 2012/0123405 A1 | 5/2012 | Moua et al. |
| 2012/0123409 A1 | 5/2012 | Tani et al. |
| 2012/0150165 A1 | 6/2012 | Conley et al. |
| 2012/0202388 A1 | 8/2012 | Selig et al. |
| 2012/0232553 A1 | 9/2012 | Bloom et al. |
| 2012/0310229 A1 | 12/2012 | Gregg |
| 2013/0023874 A1 | 1/2013 | Lawes et al. |
| 2013/0066317 A1 | 3/2013 | Evans et al. |
| 2013/0079762 A1 | 3/2013 | Twomey et al. |
| 2013/0178852 A1 | 7/2013 | Allen, Iv et al. |
| 2013/0237982 A1 | 9/2013 | Rencher et al. |
| 2013/0296846 A1 | 11/2013 | Canady et al. |
| 2014/0100569 A1 | 4/2014 | Lawes et al. |

(56) References Cited

U.S. PATENT DOCUMENTS

| | | |
|---|---|---|
| 2014/0236202 A1 | 8/2014 | Palmer et al. |
| 2014/0276772 A1 | 9/2014 | Batchelor et al. |
| 2014/0276785 A1 | 9/2014 | Batchelor et al. |
| 2014/0276786 A1 | 9/2014 | Batchelor |
| 2014/0276794 A1 | 9/2014 | Batchelor et al. |
| 2014/0276795 A1 | 9/2014 | Batchelor et al. |
| 2014/0276796 A1 | 9/2014 | Batchelor et al. |
| 2014/0276797 A1 | 9/2014 | Batchelor et al. |
| 2014/0276798 A1 | 9/2014 | Batchelor et al. |
| 2014/0276799 A1 | 9/2014 | Batchelor et al. |
| 2014/0276800 A1 | 9/2014 | Batchelor et al. |
| 2014/0276804 A1 | 9/2014 | Batchelor |
| 2015/0119885 A1 | 4/2015 | Windgassen et al. |
| 2015/0148798 A1 | 5/2015 | Windgassen et al. |
| 2015/0320485 A1 | 11/2015 | Batchelor et al. |
| 2016/0051273 A1 | 2/2016 | Batchelor et al. |
| 2016/0051275 A1 | 2/2016 | Batchelor et al. |
| 2016/0051314 A1 | 2/2016 | Batchelor et al. |
| 2017/0281260 A1 | 10/2017 | Batchelor et al. |
| 2019/0125376 A1 | 5/2019 | Batchelor et al. |
| 2019/0126442 A1 | 5/2019 | Batchelor et al. |
| 2019/0126458 A1 | 5/2019 | Batchelor et al. |

FOREIGN PATENT DOCUMENTS

| | | |
|---|---|---|
| EP | 1810629 A2 | 7/2007 |
| EP | 1977706 A1 | 10/2008 |
| JP | H08322847 A | 12/1996 |
| JP | H09503423 A | 4/1997 |
| JP | H09122140 A | 5/1997 |
| JP | H1057390 A | 3/1998 |
| JP | 2000070280 A | 3/2000 |
| JP | 2000102545 A | 4/2000 |
| JP | 2001170070 A | 6/2001 |
| JP | 2004147724 A | 5/2004 |
| JP | 2012517869 A | 8/2012 |
| WO | WO-9605776 A1 | 2/1996 |
| WO | WO-9966850 A1 | 12/1999 |
| WO | WO-2006122279 A2 | 11/2006 |
| WO | WO-2007002545 A1 | 1/2007 |
| WO | WO-2010101897 A1 | 9/2010 |
| WO | WO-2014096815 A2 | 6/2014 |

OTHER PUBLICATIONS

"U.S. Appl. No. 15/801,379, Non Final Office Action mailed Aug. 19, 2021", 18 pgs.
"U.S. Appl. No. 15/801,379, Non Final Office Action mailed Sep. 10, 2020", 10 pgs.
"U.S. Appl. No. 15/801,379, Notice of Allowance mailed Mar. 9, 2022", 11 pgs.
"U.S. Appl. No. 15/801,379, Response filed Jun. 3, 2020 to Restriction Requirement mailed Apr. 3, 2020", 7 pgs.
"U.S. Appl. No. 15/801,379, Response filed Jul. 6, 2021 to Final Office Action mailed Apr. 6, 2021", 10 pgs.
"U.S. Appl. No. 15/801,379, Response filed Nov. 19, 2021 to Non Final Office Action mailed Aug. 19, 2021", 14 pgs.
"U.S. Appl. No. 15/801,379, Response filed Dec. 10, 2020 to Non Final Office Action mailed Sep. 10, 2020", 11 pgs.
"U.S. Appl. No. 15/801,379, Restriction Requirement mailed Apr. 3, 2020", 6 pgs.
"U.S. Appl. No. 15/801,533, Non Final Office Action mailed Oct. 29, 2019", 10 pgs.
"U.S. Appl. No. 15/801,533, Notice of Allowance mailed Feb. 19, 2020", 9 pgs.
"U.S. Appl. No. 15/801,533, Response filed Jan. 29, 2020 to Non Final Office Action mailed Oct. 29, 2019", 13 pgs.
"U.S. Appl. No. 15/801,583, Final Office Action mailed Feb. 16, 2021", 11 pgs.
"U.S. Appl. No. 15/801,583, Final Office Action mailed Jul. 16, 2021", 9 pgs.
"U.S. Appl. No. 15/801,583, Non Final Office Action mailed Jan. 7, 2020", 14 pgs.
"U.S. Appl. No. 15/801,583, Non Final Office Action mailed Feb. 16, 2021", 11 pgs.
"U.S. Appl. No. 15/801,583, Non Final Office Action mailed Jul. 28, 2020", 12 pgs.
"U.S. Appl. No. 15/801,583, Notice of Allowance mailed Dec. 15, 2021", 12 pgs.
"U.S. Appl. No. 15/801,583, Response filed Apr. 7, 2020 to Non Final Office Action mailed Jan. 7, 2020", 11 pgs.
"U.S. Appl. No. 15/801,583, Response filed May 17, 2021 to Non Final Office Action mailed Feb. 16, 2021", 13 pgs.
"U.S. Appl. No. 15/801,583, Response filed Oct. 15, 2021 to Final Office Action mailed Jul. 16, 2021", 9 pgs.
"U.S. Appl. No. 15/801,583, Response filed Oct. 28, 2020 to Non Final Office Action mailed Jul. 28, 2020", 12 pgs.
"U.S. Appl. No. 15/801,583, Supplemental Notice of Allowability mailed Mar. 2, 2022", 3 pgs.
"Lindstrom Ergonomic Pliers, Flat Nose, Smooth Jaw- RX 7490", Amazon, (Accessed Oct. 2, 2015), 5 pgs.
"Red Thumb Clamp 323C Zipper Clip with a Sharp Nose Pliers", Aliexpress, (Oct. 2, 2015), 5 pgs.
"Revlon Cuticle Nipper Full Jaw #38210", ebay, (Accessed Oct. 2, 2015), 3 pgs.
"Seki Edge Flat Slant Tip Cuticle Nipper from Seki Edge", Amazon, (Accessed Oct. 2, 2015), 5 pgs.
Batchelor, Kester, et al., "Bias Device for Biasing a Gripping Device By Biasing Working Arms Apart", Potentially related U.S. Appl. No. 15/801,379, filed Nov. 2, 2017, 24 pgs.
Batchelor, Kester, et al., "Bias Device for Biasing a Gripping Device Including a Central Body and Shuttles On the Working Arms", Potentially Related U.S. Appl. No. 15/801,583, filed Nov. 2, 2017, 29 pgs.
Batchelor, Kester, et al., "Bias Device for Biasing a Gripping Device With a Shuttle On a Central Body", Potentially Related U.S. Appl. No. 15/801,533, filed Nov. 2, 2017, 38 pgs.
Batchelor, Kester, et al., "Combination Electrosurgical Device", Potentially related U.S. Appl. No. 14/210,741, filed Mar. 14, 2014, 38 pgs.
Batchelor, Kester, et al., "Combination Electrosurgical Device", Potentially related U.S. Appl. No. 14/211,042, filed Mar. 14, 2014, 38 pgs.
Batchelor, Kester, et al., "Combination Electrosurgical Device", Potentially related U.S. Appl. No. 14/206,010, filed Mar. 12, 2014, published as 2014/0276797, 78 pgs.
Batchelor, Kester, et al., "Combinationelectrosurgical Device", Potentially related U.S. Appl. No. 14/205,598, filed Mar. 12, 2014, (Mar. 12, 2014), 51 pgs.
Batchelor, Kester, et al., "Combinationelectrosurgical Device", Potentially related U.S. Appl. No. 14/205,919, filed Mar. 12, 2014, 51 pgs.
Batchelor, Kester, et al., "Combinationelectrosurgical Device", Potentially related U.S. Appl. No. 14/210,535, filed Mar. 14, 2014, 38 pgs.
Batchelor, Kester, et al., "Electrosurgical Instrument", Potentially related U.S. Appl. No. 14/177,780, filed Feb. 11, 2014, 24 pgs.
Batchelor, Kester, et al., "Electrosurgical Instrument", Potentially related U.S. Appl. No. 14/178,411, filed Feb. 12, 2014, 24 pgs.
Batchelor, Kester, et al., "Hand Switched Combined Eletrosurgical Monopolar and Bipolar Device", Potentially related U.S. Appl. No. 14/209,071, filed Mar. 13, 2014, 19 pgs.
Batchelor, Kester, et al., "Multi-Mode Combination Electrosurgical Device", Potentially related U.S. Appl. No. 14/830,255, filed Aug. 19, 2015, 35 pgs.
Batchelor, Kester, et al., "Offset Forceps", Potentially related U.S. Appl. No. 14/178,569, filed Feb. 12, 2014, 29 pgs.
Batchelor, Kester, et al., "Offset Forceps", Potentially related U.S. Appl. No. 14/178,577, filed Feb. 12, 2014, 29 pgs.
Batchelor, Kester, et al., "Surgical Forceps and Latching System", Potentially related U.S. Appl. No. 14/829,725, filed Aug. 19, 2015, 30 pgs.
Giuiliani, Thomas, "Reconfigurable Electrosurgical Device", Potentially related U.S. Appl. No. 14/830,069, filed Aug. 19, 2015, 34 pgs.

(56) References Cited

OTHER PUBLICATIONS

Windgassen, Ryan, et al., "Combination Electrosurgical Device", Potentially related U.S. Appl. No. 14/589,515, filed Jan. 5, 2015, 57 pgs.
Windgassen, Ryan, et al., "Combinationelectrosurgical Device", Potentially related U.S. Appl. No. 14/589,482, filed Jan. 5, 2015, 51 pgs.

\* cited by examiner

BIAS DEVICE FOR BIASING A GRIPPING DEVICE BY BIASING WORKING ARMS APART

This application is a continuation of U.S. patent application Ser. No. 15/801,379, filed Nov. 2, 2017, which is incorporated by reference herein in its entirety.

FIELD

The present teachings generally relate to a bias device that selectively biases the arms of a gripping device and preferably a surgical device that is a combination device, which is configured as forceps.

BACKGROUND

Typically, gripping devices such as forceps include a hinge that connects the arms together so that the arms are movable relative to each other. The hinge may allow the gripping devices to move so that the gripping devices are movable to an open position where the arms of the forceps are moved apart and upon an application of a closing force the arms of the gripping devices are moved into a closed position where an item of interest can be gripped within the gripping device. Other gripping devices such as pliers, nail cutters, cuticle nippers, or the like have added features that extend between the arms and create a direct force on both of the arms so that the arms are biased open. These devices always bias the arms apart and cannot be disconnected. Some attempts have been made to create a device that is disengageable by pivoting the device from an "on" position to an "off" position or by adding a device that is removable. However, these devices may become lost or damaged over time such that the application of force is changed or is not possible. Further, these devices impart a force directly on both of the arms so that the arms are directly moved apart by the feature.

Examples of some gripping devices such as pliers and cuticle nippers that include a feature that generates a force may be found in U.S. Pat. Nos. D386,054; 5,619,892; and 8,555,754 all of which are incorporated by reference herein for all purposes. It would be attractive to have a gripping device including a bias device that is selectively engageable. It would be attractive to have a gripping device with bias device that is engageable and disengageable without removing the bias device form the gripping device or moving the bias device on or along the gripping device. What is needed is a bias device that can be activated and deactivated with one hand. What is needed is a bias device that may apply a force to one arm individually or two or more arms. It would be attractive to have one or more bias devices where a force generated by the one or more bias devices is variable.

SUMMARY

The present teachings provide: a device comprising: (a) a first working arm; (b) a shuttle located on the first working arm, and (c) a bias device; wherein the bias device biases the first working arm when the shuttle is in a first position, and wherein the bias device is free of biasing the first working arm when the shuttle is in a second position.

The present teachings meet one or more of the present needs by providing: a device comprising: (a) a first working arm; (b) a shuttle, and (c) a bias device; wherein the bias device biases the first working arm when the shuttle is in a first position, and wherein the bias device is free of biasing the first working arm when the shuttle is in a second position.

The present teachings provide: a device comprising: (a) a first working arm; (b) a second working arm; (c) a shuttle, and (d) a bias device; wherein the bias device biases the first working arm away from the second arm with a first force when the shuttle is in a first position, and wherein the bias device biases the first working arm away from the second arm with a second force when the shuttle is in a second position.

The present teachings provide: a device comprising: (a) a first working arm; (b) a second working arm; (c) a shuttle; and (d) a bias device located on the first working arm; wherein the bias device biases the first working arm away from the second arm with a first bias force when the shuttle is in a first position, and wherein the bias device biases the first working arm away from the second arm with a second bias force or no force when the shuttle is in a second position, and the first bias force is greater than the second bias force.

The present teachings provide: a device comprising: (a) a first working arm; (b) a second working arm; (c) a shuttle; and (d) a bias device located on the shuttle; wherein the bias device biases the first working arm away from the second working arm with a first bias force when the shuttle is in a first position; and wherein the bias device biases the first working arm away from the second working arm with a second bias force when the shuttle is in a second position, and the first bias force is greater than the second bias force.

The present teachings provide: a device comprising: (a) a first working arm; (b) a second working arm; (c) a shuttle; (d) a bias device located on the first working arm; and (e) a recess located within the second working arm; wherein the shuttle covers the recess when the shuttle is in a first position so that the bias device biases the first working arm away from the second working arm with a first bias force; and wherein the recess is exposed when the shuttle is in a second position so that the bias device extends into the recess so that the bias device biases the first working arm away from the second working arm with a second bias force or the bias device is free of creating a bias force.

The teachings provide a gripping device including a bias device that is selectively engageable. The teachings provide a gripping device with bias device that is engageable and disengageable without removing the bias device form the gripping device or moving the bias device on or along the gripping device. The teachings provide a bias device that can be activated and deactivated with one hand. The teachings provide a bias device that may apply a force to one arm individually or two or more arms. The teachings provide one or more bias devices where a force generated by the one or more bias devices is variable.

DETAILED DESCRIPTION

Figure 1:
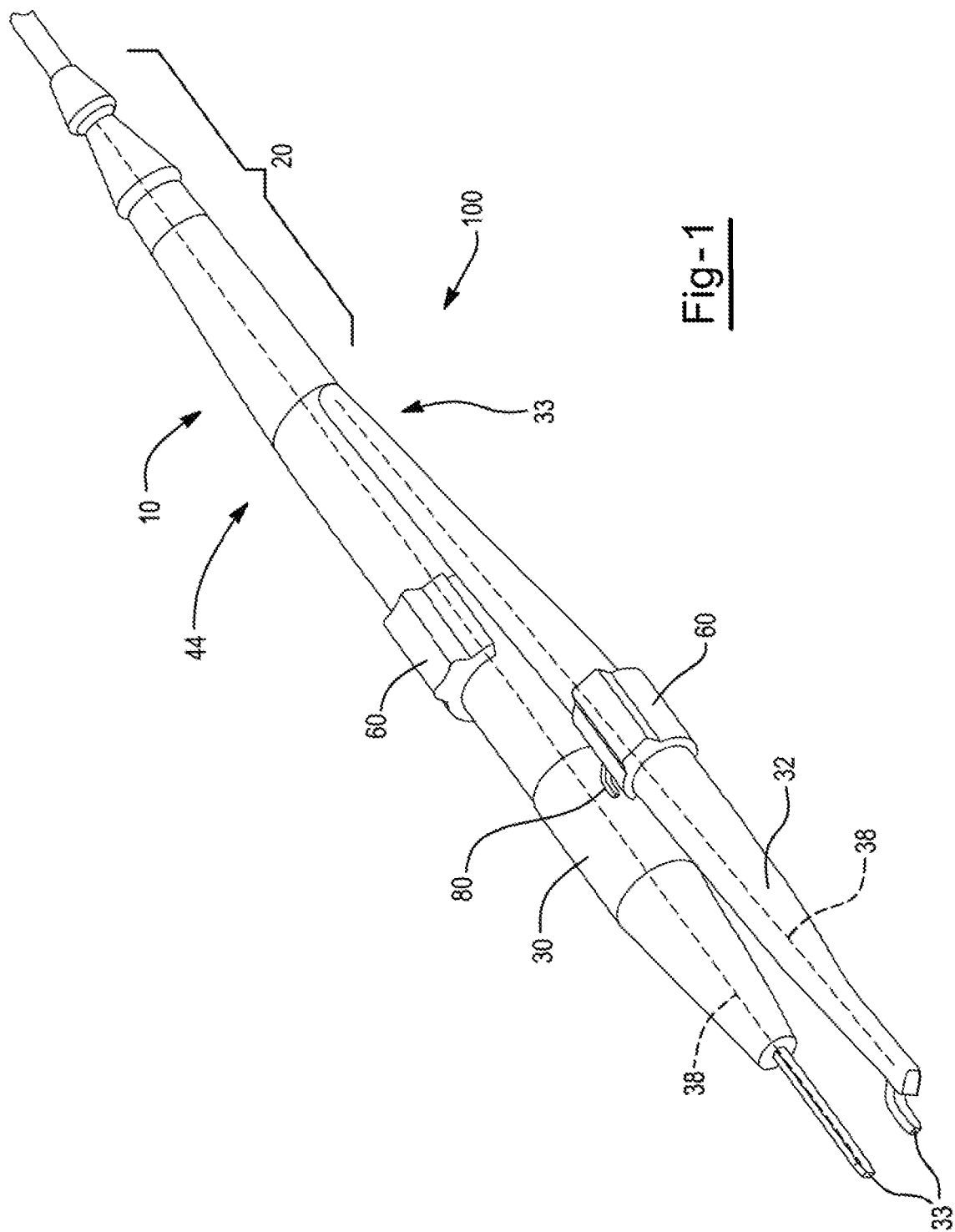
FIG. 1 is a perspective view of an electrosurgical device.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings relate to an instrument. The instrument may function to grip one or more objects of interest. Preferably, the instrument is a gripping device. More preferably, the instrument is forceps. Most preferably, the gripping device is surgical forceps. The instrument may be forceps, tweezers, scissors, retaining ring tool, or a combination thereof. The instrument may function to grip, hold, squeeze, or a combination thereof one or more objects. The instrument may include one or more finger grips (i.e., configured like scissors) that may be used to move the instrument so that the instrument may be used to grip one or more objects. The instrument may be free of finger grips and be actuated by direct pressure being applied to opposing sides of the forceps so that the instrument closes and grips an object. The instrument may have working arms that cross and form an X shape. The instrument may be opened when a distal end of a first working arm is moved towards a distal end of a second working arm. The instrument may be closed when a distal end of a first working arm is moved towards a distal end of a second working arm. For example, the first working arm and the second working arm may be moved apart but the distal ends may be opened when the working arm and the distal ends are colinear, but when the distal ends cross an opposing working arm the distal ends may be biased closed. The first working arm and the second working arm may move laterally, within a plane, or both (e.g., perpendicular to a longitudinal axis). Preferably, the first working arm and the second working arm move towards and away from each other without rotating, moving out of a plane, or both. The instrument has a distal end and a proximal end. The instrument may have working arms that are generally straight. The instrument includes at least two working arms.

The working arms may function to grip, hold, squeeze, or a combination thereof an object when the object is between the two or more opposing working arms. The working arms include a proximal end and a distal end. The proximal end may be in contact with a body, a handle, or both. The first working arm and the second working arm may converge together at their respective proximal ends, at the handle, the body, or a combination thereof. The distal end may include one or more electrodes, one or more tips, or both for applying a therapy current, a gripping force, or both. The working arms may include one or more gripping features that may assist in gripping, holding, squeezing, or a combination thereof an object. The instrument may include two or more working arms. Preferably, the instrument includes at least two working arms. The instrument may include three or more, four or more, five or more, or even six or more working arms. More preferably, the instrument only includes two working arms. The working arms may all be substantially identical. When only a first working arm and a second working arm are present the first working arm and the second working arm may be mirror images of each other. When only a first working arm and a second working arm are present the instrument is configured as forceps.

The working arms, forceps, electrosurgical device, or a combination thereof may be movable between at least a first position and a second position. For example, in the second position the working arms are immobilized so that the working arms cannot be used a forceps. The working arms may be longitudinally static and moveable relative to each other (e.g., laterally within a plane). The working arms may be longitudinally moveable and may be moveable relative to each other (e.g., laterally movable) so that a gripping force may be created. Preferably, the working arms may be movable laterally relative to each other (i.e., towards and away from each other within a single plane). The working arms may not be rotatable. The working arms may rotate about a pivot or a pivot pin to grip or create a force. A pin may connect a first working arm and a second working arm and the pin may be the pivot point. The working arms may be movable about a pivot point so that as one end of the working arms are moved closer together (e.g., a proximal end) an opposing end is moved further apart (e.g., a distal end). The working arms may each have a pivot point. The working arms may extend cantilever and may pivot about a cantilever connection with the body, the handle, the gripping portion, or a combination thereof. The working arms may be retractable and/or extendable individually, simultaneously, or both. The working arms may be selectively retractable and/or extendable so that one or more tip regions are exposed. The working arms may be rigid. The rigid working arms may rotate about a pivot or a pin to create a gripping force. The working arms may be connected to each other, a body portion, or both by a pin that extends through a pivot and the working arms may rotate about the pivot to create a gripping force. The working arms may include one or more cross overs.

The one or more cross overs may function to change the forceps from a bias open device to a bias closed device. The cross overs may be where the working arms cross each other so that a distal end of the working device is located on an opposing side of the forceps as a working arm that it was connected, a proximal end, or both. The cross over may have one working arm passing over or under another working arm. The cross over may have a portion of one working arm passing through another working arm. The cross over may form an X shape. The cross over may be located on an opposite end of the arms as the one or more bosses, the pivot point, or both.

The working arms may include one or more bosses that a pin extends through to connect the working arms to body so that a pivot point is created. Preferably, each working arm includes at least two bosses and the bosses extend on both sides of a portion of the body and the pivot pin extends through the bosses and a portion of the body to connect the arms to the body. The pivot pin may movably connect the working arms to a body. The pivot point may create a hinge. A single pivot pin may connect more than one working arm. For example, the working arms may be connected together by a single pivot pin. Each working arm may be connected individually by a pivot pin. The connection may form a joint. The joint may be a pivot joint, a cantilever joint or both. Each working arm may include a joint. Both working arms may be connected by a single joint. The bias device may be located on a distal side of the joint or the proximal side of the joint. The first working arm, second working arm, and body may all be part of the joint. The first working arm and body and the second working arm and body may form a joint. The pivot pin may be made of any material that permits the working arms to rotate. For example, the pivot pin may be plastic, metal, stainless steel, surgical steel, or a combination thereof. The working arms may be free of a pivot pin. For example, a first working arm may extend over (e.g., cross-over or cross-under) a second working arm so that the distal end is located on an opposite side of the forceps and the proximal end. The cross-over/cross-under may create a device that opens upon an application of force. The working arms may be flexible and may flex to open and close. For example, the working arms may be constrained (at one end) and upon release of the constraint the working arms may flex open. The working arms may be movable between two or more positions. Preferably, the working arms are movable between at least a first position (e.g., open) and a second position (e.g., closed). The working arms may be movable between a bipolar configuration (e.g., first position) and a monopolar configuration (e.g., second position). The working arms may be movable between an open position (i.e., first position) and a closed position (i.e., second position). The working arms in the first position may be off, energized, one working arm may be energized, or a combination thereof. The working arms in the second position may be off, one or both of the working arms may be electrically disconnected, one or both of the working arms may be electrically connected, one working arm may be shorted by the other working arm, or a combination thereof. The working arms may be moved between one or more positions by a user applying a force to a gripping portion.

The gripping portion may function to open the working arm, close the working arms, allow a user to manipulate the forceps, or a combination thereof. The gripping portions may move the working arms when a force is applied to the working arms. The gripping portions may be located at the proximal end or the distal end of each of the working arm. The gripping portion may be located proximate to the handle, the body, or both. The gripping portion of the working arms may extend over the handle, the body, or both. The gripping portions may extend along the handle, the body, or both. The gripping portions may be located opposite a tip region of the working arms. The gripping portions may be located at a proximal end and the tip region may be located at a distal end.

The working arms may include a tip region. The tip region may include a portion that is configured to assist in facilitating gripping, holding, squeezing, or a combination thereof. The tip region may be located at the distal most end (i.e., an end of the instrument furthest from the user) of the working arms. The tip regions when moved towards each other may grip an object of interest between the two working arms (e.g., tissue). Additionally, the tip region may be configured in one or more electrosurgical configurations (e.g., a monopolar configuration, bipolar configuration, or a combination of both). The tip region may include teeth, serrations, mouse teeth, be free of teeth (i.e., smooth), or a combination thereof. The tip region may be fully and/or partially insulated. Preferably, the tip region includes insulation on the non-contact portions of the working arms so that electrosurgical energy is not transferred through incidental contact. The tip region may include or may be an active portion (e.g., an electrode), an inactive portion (e.g., an insulated portion), or a combination of both.

The electrode may function to provide a therapy signal (e.g., current, voltage, power, electricity, or a combination thereof) to a location of interest. The electrode may be electrically conductive so that the instrument is an electrosurgical device. The electrode may transmit a therapy signal between the working arms, from a working arm to the blade, from a working arm to the blade electrode, from one or both working arms to a ground pad, or a combination thereof. The electrode may both provide power and a contact surface for gripping and holding an item of interest. The electrode may be connected to an electrical path that provides a therapy signal from the body, a generator, or both to a location of interest.

The electrical path may function to provide a therapy signal to a feature or location of interest. The electrical path may extend along one or more of the working arms. The electrical path may be one or more structures that when connected together provide a path for power to flow through the instrument. The electrical path may be engageable and disengageable. The electrical path may extend from a handle, gripping portion, body, or a combination thereof to the working arms (e.g., first working arm, second working arm, or both. The first working arm, the second working arm, or both may be mechanically moved to form a blade.

The blade may function to mechanically cut, electrically cut, electrically coagulate, apply a therapy current, or a combination thereof. The blade may be any device that may be used to apply monopolar power during a procedure, that may be longitudinally movable, rotationally movable, extendable, retractable, or a combination thereof. The blade may be movable along or relative to a handle, a body, a gripping portion, or a combination thereof. The blade may be connected to and extend from a handle, a body, a gripping portion or a combination thereof. The blade may be static. Preferably, in one embodiment the blade may be static and the working arms moved relative to the blade so that when the working arms are moved the blade is exposed. More preferably, the blade is a movable. The blade may have one or more positions. The blade may have a plurality of positions. The blade may have a first position (e.g., retracted), a second position (flush), and a third position (e.g., extended). The blade may be formed by retracting one of the working arms. The first position may be where the blade is located relative to a working arm so that one working arm (e.g., the blade) extends past another working arm (e.g., a working arm is retracted so that a second working arm is extend past the retracted working arm). The first position may be where the blade is electrically connected, electrically in communication with another handpiece component, or a both. The second position may be where a distal end of the blade (i.e., second working arm) is flush with the distal end of the first working arm. The third position may be where the blade is located relative to the first working arm so that the blade is retracted relative to the first working arms (e.g, the blade is retracted so that the blade is located proximate to the user). The second position and/or first position may be where the blade is electrically connected, supplies a therapy current, is electrically continuous, or a combination thereof. The blade may be a separate piece that when activated may be used to supply monopolar power. The blade may be formed by connecting the two working arms together and supplying power through only one working arm. The blade may be formed by retracting one working arm so that only one working arm is extending distally. The blade may be used for electrically cutting, mechanically cutting, or both. The blade may be a discrete third working arm that may extend from one of the working arms. The electrosurgical device may be free of a blade. The blade may include a blade electrode. The blade electrode may supply a therapy current to a location of interest. The blade electrode may contact tissue so that a therapy current is supplied from the blade electrode to the first working arm. One or more shuttles may move relative to the blade, along the blade, parallel to the blade, or a combination thereof.

The one or more shuttles may function to activate or deactivate one or more functions of the instrument, move one or more components of the instrument, obstruct one or more buttons of the instrument, move a bias device, move a deactivation feature, deactivate a deactivation feature, align a bias device and deactivation feature, align a bias device and a contact zone, or a combination thereof. The one or more shuttles may move independent of the first working arm, the second working arm, the blade, the body, or a combination thereof. For example, if the blade is longitudinally movable, a shuttle located on the body may move longitudinally without the blade moving or vice versa. The electrosurgical device may include one or more shuttles, two or more shuttles, three or more shuttles, four or more shuttles, or even five or more shuttles. For example, there may be three shuttles on the body, one that moves the blade and two that move along the body to activate and deactivate bias, and each working arm may include a shuttle. Each working arm may include one or more shuttles. The body, blade, or both may include one or more shuttles. The body may include two shuttles or even three shuttles. The shuttles may function to carry one or more bias devices. The shuttle may function to carry one or more deactivation features. The shuttles may function to provide a contact zone or contact location for one or more bias devices. The shuttles may only have one or more bias devices, one or more deactivation features, one or more contact zones, or a combination thereof on one side. For example, a shuttle may only face a first side of a body or a first working arm. The shuttle may have two sides and each side may include one or more deactivation features, one or more bias devices, one or more contact zones, or a combination thereof. The shuttles may include two or more bias devices, contact zone, deactivation features, or a combination thereof on each side so that as the shuttle is longitudinally moved the amount of force created may be varied based upon the distance of the shuttle from pivot point, body, or both. The shuttle may have two or more pieces. The shuttle may be a plurality of pieces. The shuttle may have a first shuttle first portion, a first shuttle second portion, a third shuttle portion, a fourth shuttle portion, or a combination thereof. For example, two shuttle portions may be located on the body and the two shuttle portions may be moved as one shuttle or moved as two discrete shuttles. Three shuttles may be located on the body. The three shuttles may be a first shuttle first portion and a first shuttle second portion and a second shuttle portion. The first shuttles may control bias and the second shuttle may control the blade position. A first shuttle first portion may be located on a first working arm and a first shuttle second portion may be located on a second working arm. A first shuttle portion may be located on a first side of the body and a second shuttle portion may be located on a second side of the body. The shuttle may be movable between a plurality of positions. The one or more shuttles may be movable between one or more positions. Preferably, the shuttle is movable between at least a proximal position (e.g., first position) and a distal position (e.g., second position). The shuttle may retract and extend the blade, a working arm, or both. For example, the shuttle may extend a blade out of one or both of the working arms. The shuttle may engage and disengage one or more bias devices. The shuttle may cover, expose, or both one or more deactivation features, one or more buttons, or both. Each shuttle may include two or more positions, three or more positions, four or more positions, or even five or more positions. The shuttle may move along one or more of the working arms. The shuttle may engage the bias device. The shuttle may engage the bias device when the shuttle is in the first position, the second position, the third position, the fourth position, or a combination thereof. The shuttle may be free of engagement with the bias device when the shuttle is in the first position, the second position, the third position, the fourth position, or a combination thereof. The shuttle may have one or more contact zones that are contacted by the bias devices.

The one or more contact zones may function to create a contact surface for the bias device to contact. The one or more contact zones may function to assist is biasing the working arms. The one or more contact zones may be any area of the instrument where the bias device contacts to create a bias force. The one or more contact zones may be a region of the shuttle, the one or more of the working arms, or both that assists in biasing the working arms. For example, the bias device may be connected to the working arms and may contact a contact zone of the shuttle. In another example, the bias device may be connected to a shuttle and may contact a contact zone of the working arms. The one or more contact zones may either engage the bias device or be free of engagement with the bias device. The one or more contact zones may be generally planar. The one or more contact zones may have one or more steps that extend in different planes so that contact with each step varies the amount of force created by the bias device. For example, movement of a shuttle or a bias device may move from a first step to a second step or even a third step which may increase or decrease an amount of force created by the bias device. The one or more steps may change the thickness of the shuttle so that compression of the bias device varies the amount of generated by the bias device. When steps are present the shuttle may have a position that corresponds to each of the steps. The force may be sufficiently low so that finger pressure may overcome the force to bias the working arms. The force may be about 1 Kg or more, about 2 Kg or more, about 5 Kg or less, or about 3 Kg or less (i.e., between about 0.5 Kg and about 2 Kg). The amount of force may be varied by moving one or more shuttles, bias members, or both toward a distal end, towards a proximal end, towards a pivot point, towards a cross over, a combination thereof. The shuttle may be distally or proximally moved to vary the bias force provided to each working arm depending upon a longitudinal location of the shuttle. The bias device may provide a force that is close to zero but greater than a zero bias force. The shuttle may have a distal position, a first position, a second position, a third position, a proximal position, or a combination thereof. The contact zones may have one or more recesses so that when a portion of a bias device (e.g., a free end or contact portion) contacts the contact zone the bias device and shuttle form at least a temporary connection. The one or more recesses may substantially prevent the bias device from moving (e.g., sliding) along the contact zone (e.g., the bias device may move 1 mm or less relative to the contact zone). The contact zone may be curved, include a detent, be flat, disc shaped, or a combination thereof. The contact zone may be moved so that the bias device is free of contact with the shuttle and the bias device is disabled.

The one or more bias devices may function to move one or more of the working arms. The bias device may bias one or more of the working arms open (i.e., away), one or more of the working arms closed (i.e., towards), or both. The bias devices may move the ends of the working arms towards the body, the blade or both. The bias devices may move the ends of the working arms away from the body, the blade, or both. The bias device may bias one or more of the working arms off of a body, a shuttle, a handle, an inner shell, a contact zone, or a combination thereof. The bias device may be free of providing a bias (e.g., the bias device may be disabled, turned off, or both). The one or more bias devices may be free of contact with a working arm, shuttle, body, contact zone or a combination thereof when the shuttle is in the second position. The bias device may longitudinally movable (e.g., along a length of the electrosurgical device), laterally movable (e.g., move with a working arm along a plane that is at an angle relative to the length (e.g., perpendicular)), rotationally movable (e.g., around a working arm), or a combination thereof. The bias device may be longitudinally static. The bias device may be fixed to a working arm, body, shuttle, first shuttle portion, second shuttle portion, third shuttle portion, handle, gripping portion, or a combination thereof. The bias device may be made of plastic, metal, rubber, or a combination thereof. The bias device may extend between a first working arm and the body, a second working arm and the body, or both. Depending on the position of the shuttle the bias device may be opposing a working arm or a body. The bias device may be made of an elastic material. The bias device may include elastomeric characteristics. The bias device may be a spring. The bias device may be a leaf spring, a cantilever spring, a helical spring, compression spring, a coil, a helical extension, or a combination thereof. The bias device may include one or more constrained ends, one or more free ends, one or more contact portions, or a combination thereof.

The one or more constrained ends may function to connect the bias device to a part of an instrument. The one or more constrained ends may permanently connect the bias device to a part of an instrument. The one or more constrained ends may removably connect the bias device to a part of an instrument. Preferably, the constrained ends may be connected to a working arm or a shuttle. The one or more constrained ends may be a single constrained end. The one or more constrained ends may be located on opposing ends of the bias device. For example, two opposing ends of the bias device may be constrained and a middle section may extend outward to provide the bias. The one or more constrained ends may not be an end but may constrain the bias device between to a part of the instrument at a location between the ends. For example, a central section may be constrained and two portions may extend outward from the constrained central section. The one or more constrained ends preferably are located at an end that is towards the distal end of the device. For example, the bias device may include a distal end and a proximal end and the constrained end may be the distal end of the bias device. The constrained end may be connected to a working arm, the shuttle, or both. The first working arm and the second working arm may each be connected to a constrained end of a bias device. The bias device may extend outward from the constrained end. For example, the bias device may extend from a constrained end on a first working arm towards a second working arm. The constrained end may form a cantilever connection. The bias device may only be connected at the constrained end and may include a free end that is not constrained to any part of the instrument (i.e., the working arms or the shuttle).

The free end may function to contact one or more parts of the instrument to create a bias force. The free end may extend away from the constrained end but may be free of contact with another part of the instrument to create the bias force. For example, the free end may extend outward and contact the same part as the constrained end (e.g., an arm or shuttle) and a contact surface between the free end and the constrained end may create the bias force. The free end may extend towards the same part of the instrument as the bias device (e.g., the shuttle or a working arm). Preferably, the free end contacts a contact zone and assists in creating the bias force. The free end may move along a portion of the instrument as the contact portion is biased. The free end may be in contact with a part of the instrument and move as the working arms are moved towards each other. The free end may be substantially static during movement of the working arms towards each other so that energy is stored within the bias device. The free end may be opposite a constrained end (e.g., cantilever connection). The free end may be in the same plane as the constrained end. The free end may be in a different plane than the constrained end. The bias device may include more than one free end. For example, the bias device may include 2, 3, 4, 5, or more free ends. Preferably, the bias device includes a single free end. The free end may be flat. The free end may include a covering or another material. The free end may include an insulator, an elastomeric material, or both. The free end may be free of any other materials. The free end and the constrained end may be separated by one or more breaks.

The one or more breaks may function to store energy. The one or more breaks may function to move the bias deice from a first plane to a second plane. The one or more breaks may be one or more arcuate portion of the bias device. The one or more breaks may be one or more bends in the bias device. The one or more breaks may allow the bias device to follow the contour of the working arms, the shuttle, a portion of the instrument, or a combination thereof. The one or more breaks may be a shaped portion of the bias device. The one or more breaks may move when the working arms move towards each other and store energy and when a pressure is released the working arms may release the stored energy and bias the working arms apart. The one or more breaks extend the bias device from a constrained end towards a contact portion. The one or more breaks may strengthen a portion of the bias device. The one or more breaks may prevent one or more portions of the bias device from moving. The one or more breaks, bias device, or both may include the contact portion.

The one or more contact portions may function to contact another portion of the instrument to bias one or more of the working arms apart or bias one or more of the working arms together. Preferably, the contact portions of the bias device contact a contact zone on a working arm, the shuttle, or both. The one or more contact portions may contact a first working arm, a second working arm, a shuttle, or a combination thereof. The one or more contact portions may contact a piece adjacent to a working arm. The one or more contact portions may contact a working arm. For example, the bias device may be connected to a first working arm and the contact portion may contact the first working arm and a second working arm or a shuttle to create a bias force. The contact portion may assist in compressing a bias device so that energy is stored within the bias device. The contact portion may assist in releasing energy so that the first working arm and second working arm are moved apart. Each bias device may have one or more contact portions. Each bias device may include two or more contact portions. For example, each bias device may include a contact portion that contacts a first part of the instrument (e.g., an arm) and second part of the instrument (e.g., another arm or a shuttle). The contact portion may be a constrained end, a free end, or both. The contact portion may contact a shuttle, of the instrument. The contact portion may contact a shuttle when a shuttle is in a first position (or distal position) and may extend into a deactivation feature and be free of contact with the contact zone when the shuttle is in a second position (or proximal position).

The body may function to serve as the primary gripping region for a user. The body may connect all of the components together (e.g., the blade, working arms, shuttle, buttons, etc . . . ). The body may be or include a handle, a gripping portion, or both. The body may house electrical components, buttons, controls, or a combination thereof. The body may receive power, therapy signals, or both from a generator. The body may be connected to the working arms by a pivot pin, bosses, or both. The body may connect to a proximal end of each of the working arms. The body may extend between two or more working arms. Preferably, the working arms beyond the body and the body is not located between the first working arm and the second working arm. The working arms may pivot about the body and the body may remain substantially static. Each working arm may move relative to the body individually. The body may connect both of the working arms together so that the working arms move with each other. A blade may move in and out of the body portion. A blade may extend from the body to a location between the first working arm and the second working arm. The body may be covered by an inner shell.

The inner shell may extend around the body portion, a portion of the one or more working arms, or both. The inner shell may cover one or more surfaces, preferably two or more surfaces, and more preferably three or more surfaces. The inner shell of the body portion may function to support the shuttle, the activation buttons, connect the working arms, receive all or a portion of the bias device, receive all or a portion of the blade, or a combination thereof. The inner shell may house all of the electrical elements. The inner shell may assist in activating or deactivating one or more electrical functions of the instrument. The inner shell may function to be a piece that a user grips. The inner shell may include one or more deactivation features.

The one or more deactivation features may function to deactivate the bias device, deactivate an electrosurgical configuration, or both. The deactivation feature may be a portion of the shuttle that extends over and covers the bias device. The one or more deactivation features may be a hole or recess that extends through one or more walls of the inner shell, body portion, working arm, handle, gripping portion, shuttle, electrosurgical device, or a combination thereof. Preferably, the deactivation features are a recess that create a gap so that the bias device cannot contact a part of the device to create a bias force. The one or more deactivation features may be located in a first working arm, second working arm, first shuttle, second shuttle, or a combination thereof. One or more parts may include two or more or even a plurality of deactivation features. For example, a shuttle may include two deactivation features and two contact zones. The deactivation feature may be where the bias device is free of contact with another component or a contact zone. The deactivation feature may be where a gap is sufficiently large that the bias device is free of contact with a working arm, shuttle, body, contact zone, or a combination thereof. The one or more deactivation features may be one or more recesses, one or more openings, one or more through holes, or a combination thereof. For example, the inner shell may include a recess so that when the shuttle is in a proximal position the recess is exposed and one or both of the bias devices extend into the recess and are free of contact with the inner shell and one or both of the bias devices are deactivated. The one or more deactivation features may be a distance between a contact zone and a contact portion. For example, when the shuttle is moved from a first position, where the contact zone and the contact portion are in contact, to a second position, the contact portion may be located too far from the contact zone to create a bias force. The one or more deactivation features may be a gap that is greater than a distance between a bias device and a contact surface so that the bias device cannot create a bias force. The deactivation features may be a hole that the bias device extends into so that the bias device cannot bias. The one or more deactivation features may be located on the shuttle or in the shuttle so that when the shuttle is in one position one or both of the bias devices align with the deactivation feature and are deactivated and when the shuttle is in a different position the bias device aligns with a contact zone and is activated. Preferably, the deactivation features are aligned with the contact portions of the bias device. More preferably, the deactivation features, activation buttons, or both are covered and uncovered by the shuttle moving between positions.

The first activation button, second activation button, or both may function to enable one or more electrical configurations of the instrument. The first activation button, second activation button, or both may provide a therapy current to one or both working arms, the blade, or both. The activation buttons may allow for the instrument to be an electrosurgical device. The activation buttons may allow the instrument to be both a mechanical gripping device and an electrosurgical device.

The present teachings relate to an instrument that may include electrical elements and be an electrosurgical device. Preferably, the present teachings relate to an electrosurgical device and associated componentry that form an electrosurgical system. The electrosurgical system may be any system that includes one or more of the devices taught herein. Preferably, the electrical surgical system includes at least an electrosurgical device. The electrosurgical system may include one or more handpieces (i.e., a body) as taught herein, one or more ground pads, one or more generators, one or more electrosurgical devices, one or more adjacent handpiece components, or a combination thereof and the teachings herein of each device which are incorporated into the electrosurgical system. The electrosurgical device may be any device that may be used by a surgeon to perform a surgical procedure. The electrosurgical device may function to be switched between two or more configurations, two or more states, or both (e.g., be a combination device). For example, the electrosurgical device may be switched between a monopolar configuration, a bipolar configuration, a non-electrosurgical configuration, or a combination of the three. The electrosurgical device may be any device that may be switched between two or more configurations with one hand so that a user may switch between the configurations without the need for a second hand, without disrupting the procedure, or both. The electrosurgical device may be any device and/or configuration that may be used ambidextrously, ambidextrously switched between configurations, or both. The electrosurgical device may be used to cut, perform hemostasis, coagulate, desiccate, fulgurate, electrocautery, or a combination thereof. The electrosurgical device may be any device that includes bipolar capabilities, monopolar capabilities, non-electrosurgical capabilities, or a combination thereof. The electrosurgical device may be used in open surgery. In addition to its electrosurgical capabilities the electrosurgical device may be used for non-electrosurgical purposes. For example, the electrosurgical device may be used as forceps, tweezers, or both that may be used to grip an object, an organ, a vein, skin, tissue, the like, or a combination thereof. In another example, one or more parts of the device may include a sharp edge and may be used to cut, similar to that of a scalpel. The electrosurgical device includes a proximal end (e.g., an end proximate to a user) and a distal end (e.g., an end furthest from a user). The electrosurgical device may include a handpiece and a generator. The electrosurgical device may have one or more therapy signals that extend between the handpiece and the generator.

The one or more therapy signals may be a signal, power, continuity, or a combination thereof. The one or more therapy signals may extend from and/or to the handpiece (e.g., blade, working arms, or both). The one or more therapy signals may be formed by the handpiece, formed by the generator, or both. The electrosurgical therapy signals may be a therapy current. Preferably, the electrosurgical therapy signals indicate that a user has performed a step and a signal is being transmitted so that therapy current, energy, or both is generated. The electrosurgical therapy signals may provide a signal so that one or more therapy currents are produced and the therapy currents may be used for electrosurgery. The electrosurgical therapy signal may be a monopolar therapy signal, a bipolar therapy signal, or both. The electrosurgical therapy signal may be a monopolar therapy signal, a bipolar therapy signal, or both. The monopolar therapy signal may be any signal that has a voltage differential between a return port and an active port in the generator. The monopolar therapy signal may be any signal that when applied by the electrosurgical device extends from one pole of an electrosurgical device to another pole located at a remote location, off of the electrosurgical device, off the handpiece, or a combination thereof. The bipolar therapy signal may be any signal that has a voltage differential between two leads that are connected to the electrosurgical device, that are located in the generator, or both. The bipolar therapy signal may be any signal that when applied by the electrosurgical device extends from one component of a handpiece to another component of the handpiece (e.g., between two working arms, from a blade to one or both working arms, or both). An electrosurgical therapy signal, when the activation circuit is in the second state, may exit the handpiece so that a therapy current extends from a blade, between the first working arm and the second working arm, between the blade and one or both of the working arms, or a combination thereof. The therapy signal may be generated and conducted from the handpiece to the generator.

FIG. 1 illustrates a perspective view of an electrosurgical device 100. The electrosurgical device 100 includes a body 10 with a handle 20 and a gripping portion 44. A joint 33 is located in the gripping portion 44 that connects a first working arm 30 and a second working arm 32 extending therefrom. A shuttle 60 is located on the body 10 and on the second working arm 32. The shuttle 60 on the first working arm 30 includes a bias device 80 for biasing the first working arm 30 and the second working arm 32 apart. An electrical path 38 extends from the body 10 through the first working arm 30 and the second working arm 32 respectively to an electrode 33 for supplying a therapy current.

Figure 2A:
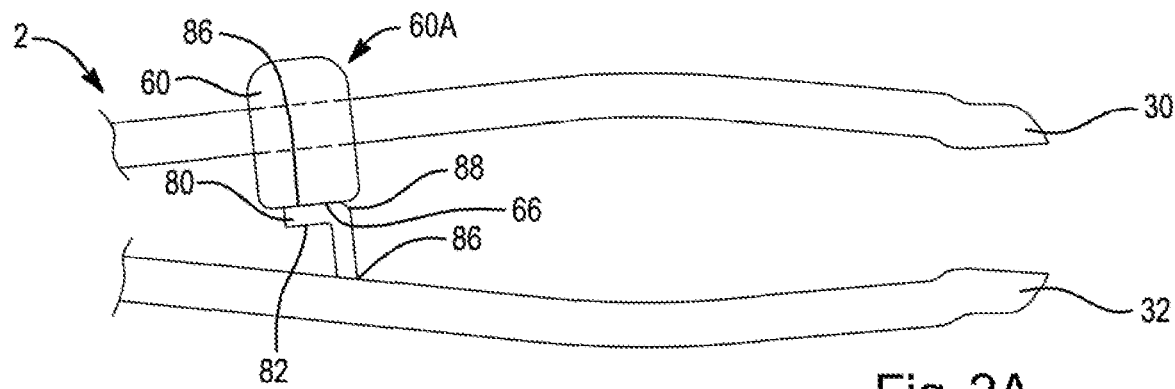
FIG. 2A illustrates a shuttle in a first position located on a first working arm and a bias device located on a second working arm.

FIG. 2A illustrates the forceps 2, bias device 80, and shuttle 60 in a first position 60A. In the first position, the bias device 80 on the second working arm 32 aligns with the shuttle 60 on the first working arm 30 so that the first working arm 30 and the second working arm 32 are biased apart. The bias device 80 includes a contact portion 86 that contacts a contact zone 66 of the shuttle 60 to create the bias force. The bias device 80 has a constrained end 86 that is connected to the second working arm 32 and a free end 82 with a break 88 located therebetween.

Figure 2B:
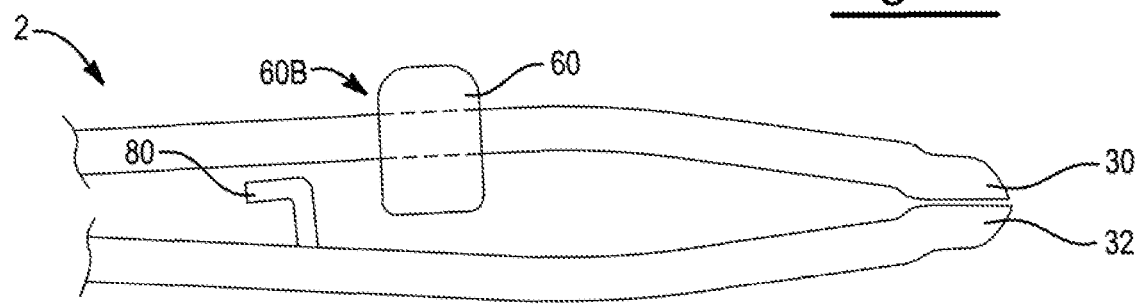
FIG. 2B illustrates a shuttle in a second position located on a first working arm and a bias device located on a second working arm.

FIG. 2B illustrates the forceps 2, bias device 80, and shuttle 60 in a second position 60B. In the second position, the bias device 80 on the second working arm 32 is misaligned with the shuttle 60 on the first working arm 30 so that the first working arm 30 and the second working arm 32 are free of biasing relative to each other.

Figure 3A:
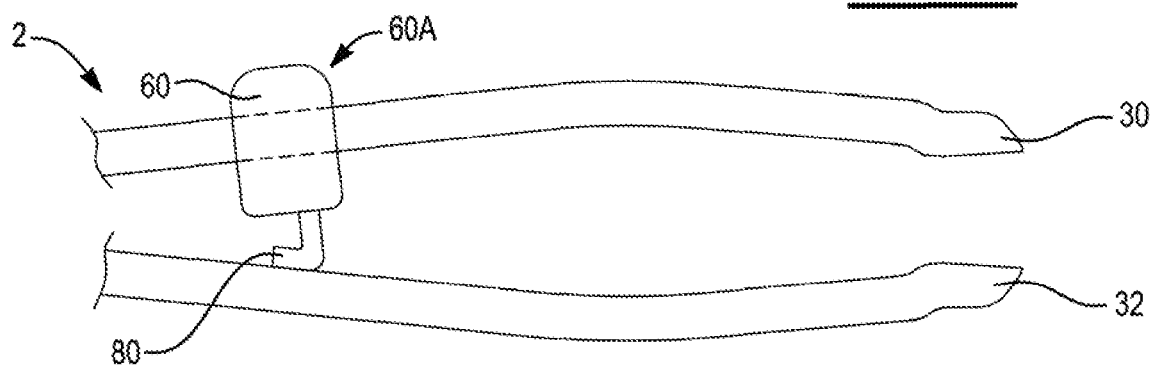
FIG. 3A illustrates a shuttle including a bias device, with the shuttle being in a first position.

FIG. 3A illustrates the forceps 2, bias device 80, and shuttle 60 in a first position 60A. The bias device 80 is located on the shuttle 60. The shuttle 60 is located on the first working arm 30 and in the first position, the shuttle 60, in the first position 60A, aligns the bias device 80 with the second working arm 32 such that the bias device 80 contacts the second working arm 32 and biases the first working arm 30 and the second working arm 32 apart.

Figure 3B:
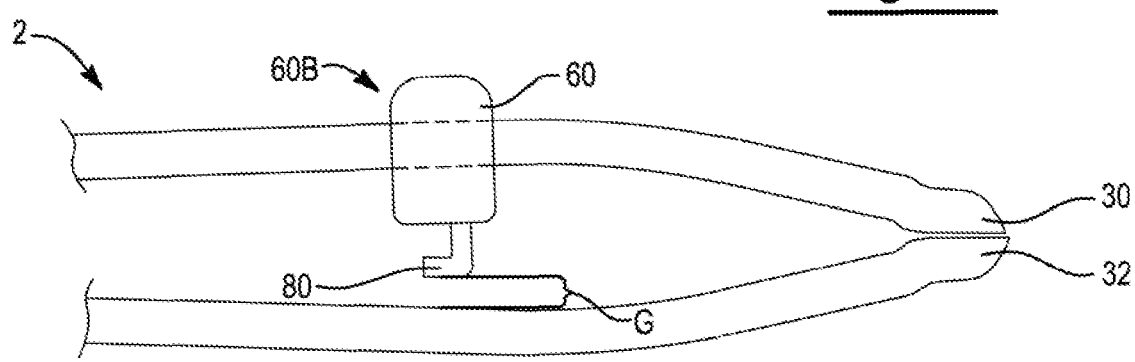
FIG. 3B illustrates a shuttle including a bias device, with the shuttle being in a second position.

FIG. 3B illustrates the forceps 2, bias device 80, and shuttle 60 in a second position 60B. The bias device 80 is located on the shuttle 60 and the shuttle 60 is moved along the first working arm 30 to the second position 60B where a gap G is located between the bias device 80 and the second working arm 32 so that the first working arm 30 and the second working arm 32 are free from biasing.

Figure 4A:
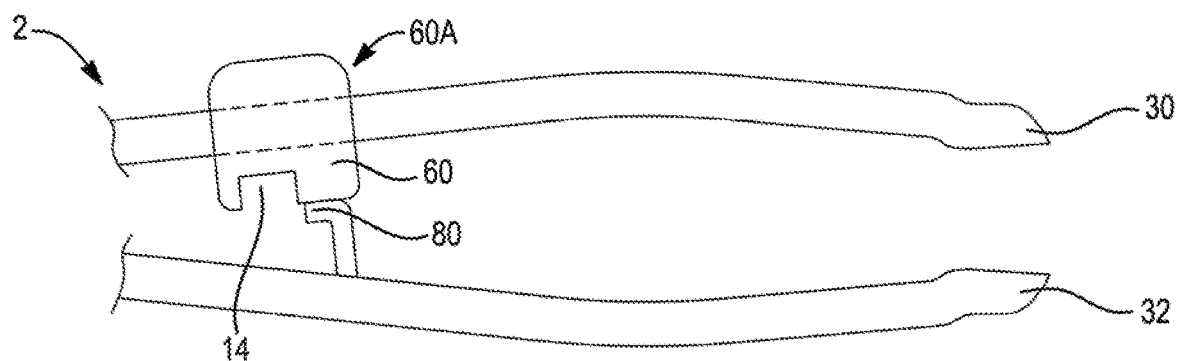
FIG. 4A illustrates a shuttle in a first position located on a first working arm and a bias device located on a second working arm, with the shuttle including a deactivation feature.

FIG. 4A illustrates the forceps 2, bias device 80, and shuttle 60 in a first position 60A. The shuttle 60 includes a deactivation feature 14 that in the first position 60A is misaligned with the bias device 80 so that the bias device 80 contacts the shuttle 60 and biases the first working arm 30 and the second working arm 32 apart. The deactivation feature 14 as shown is a recess in the shuttle 60 that prevents the bias device 80 from contacting an opposing structure.

Figure 4B:
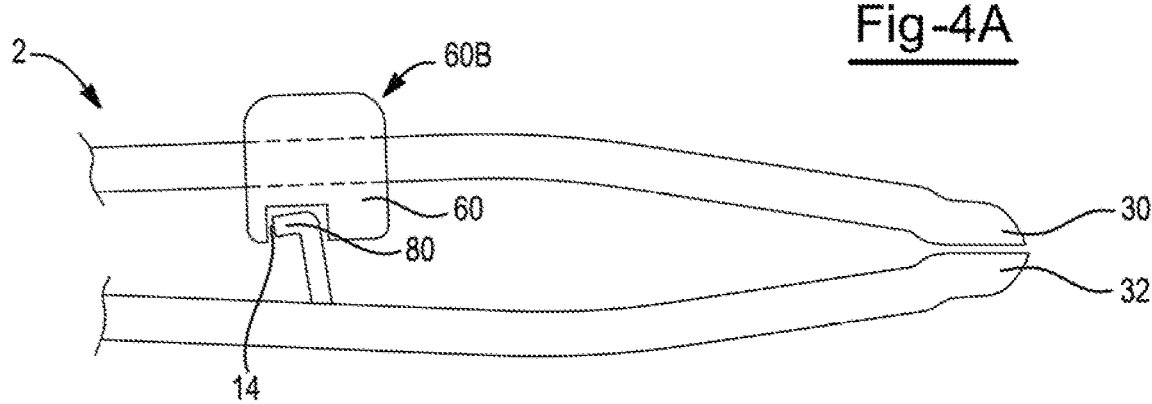
FIG. 4B illustrates a shuttle in a second position located on a first working arm and a bias device located on a second working arm, with the shuttle including a deactivation feature.

FIG. 4B illustrates the forceps 2, bias device 80, and shuttle 60 with the shuttle 60 in a second position 60B. In the second position, the deactivation feature 14 of the shuttle aligns with the bias device 80 on the second working arm 32 so that the first working arm 30 and the second working arm 32 are free of biasing relative to each other.

Figure 5A:
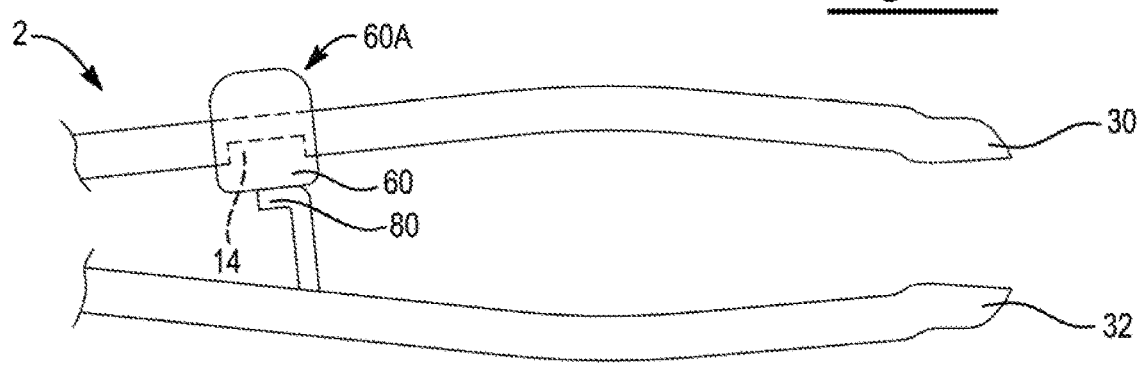
FIG. 5A illustrates a shuttle in a first position on a first working arm covering a deactivation feature with a bias device being located on a second working arm.

FIG. 5A illustrates the forceps 2, bias device 80, and shuttle 60 in a first position 60A. In the first position 60A, the shuttle 60 aligns with the bias device 80 on the second working arm 32 so that the first working arm 30 and the second working arm 32 are biased apart. A deactivation feature 14 is covered when the shuttle 60 is in the first position 60A.

Figure 5B:
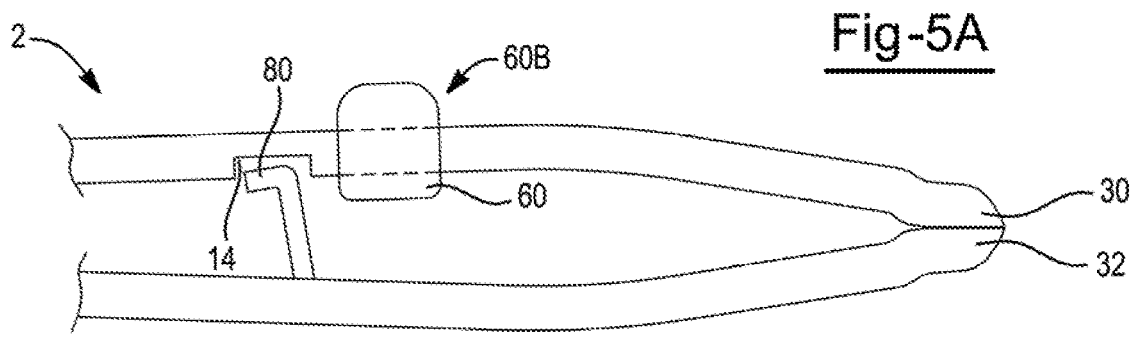
FIG. 5B illustrates a shuttle in a second position on a first working arm uncovering a deactivation feature with a bias device being located on a second working arm.

FIG. 5B illustrates the forceps 2, bias device 80, and shuttle 60 in a second position 60B. When the shuttle 60 is in the second position, a deactivation feature 14 in the first working arm 30 is uncovered and the bias device 80 on the second working arm 32 is aligned with the deactivation feature 14 so that the first working arm 30 and the second working arm 32 are free of biasing relative to each other.

Figure 6A:
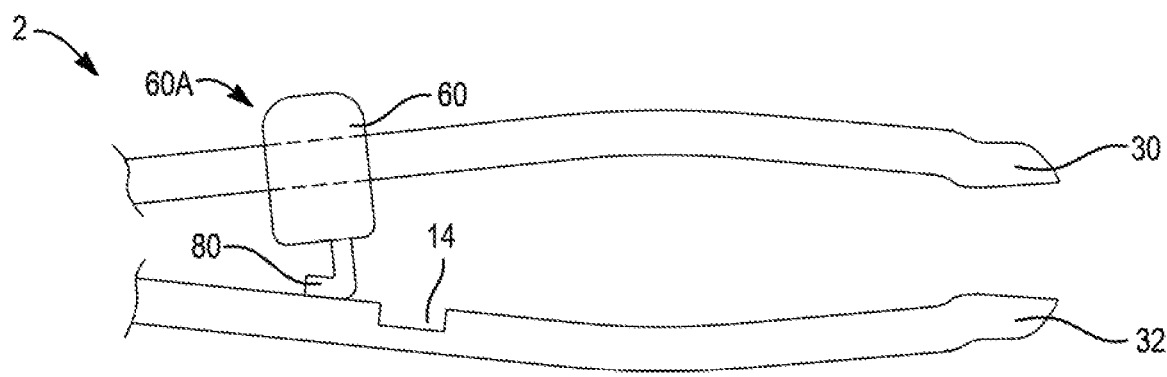
FIG. 6A illustrates forceps with a shuttle on a first working arm and a deactivating feature on a second working arm with the shuttle being in a first position.

FIG. 6A illustrates the forceps 2, bias device 80, and shuttle 60 in a first position 60A. The bias device 80 is located on the shuttle 60. The shuttle 60 is located on the first working arm 30 and in the first position, the shuttle 60, in the first position 60A, aligns the bias device 80 with the second working arm 32 such that the bias device 80 contacts the second working arm 32 and biases the first working arm 30 and the second working arm 32 apart. The bias device 80 is misaligned with a deactivation feature 14.

Figure 6B:
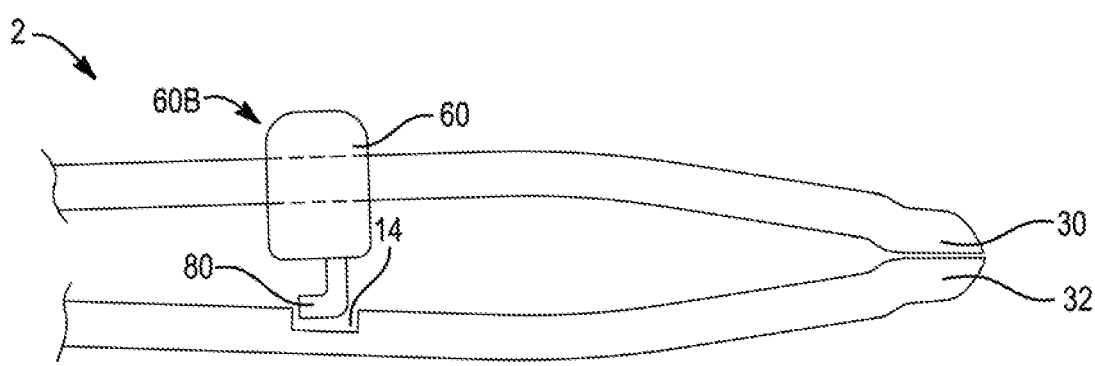
FIG. 6B illustrates forceps of FIG. 6A with the shuttle being in a second position so that the bias device is locate opposite a deactivation feature.

FIG. 6B illustrates the forceps 2, bias device 80, and shuttle 60 in a second position 60B. The bias device 80 is located on the shuttle 60 and the shuttle 60 is moved along the first working arm 30 to the second position 60B. In the second position 60B, the bias device is aligned with the deactivation feature 14 on the second working arm so that the first working arm 30 and the second working arm 32 are free from biasing.

Figure 7A:
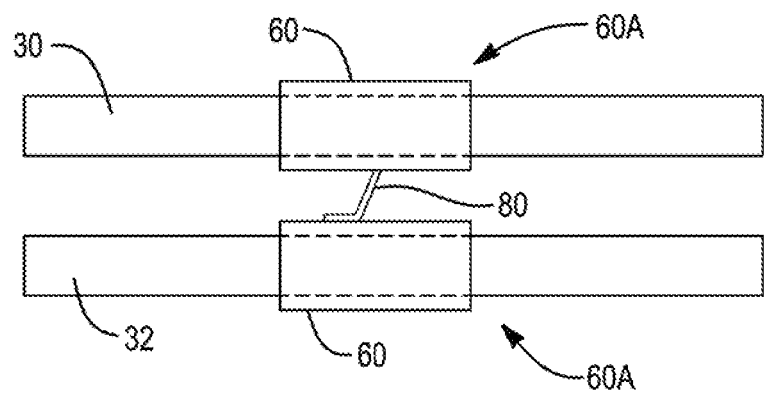
FIG. 7A illustrates forceps with two shuttles that are both in a second position.

FIG. 7A illustrates a shuttle 60 on the first working arm 30 and a shuttle 60 on the second working arm 32 with both shuttles 60 in the first position 60A. The bias device 80 located on the shuttle 60 on the first working arm is aligned with the shuttle 60 on the second working arm 32 so that the first working arm 30 and the second working arm 32 are biased apart.

Figure 7B:
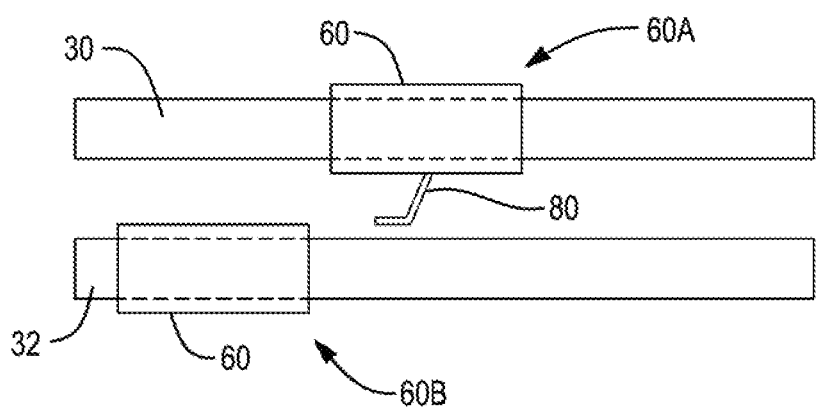
FIG. 7B illustrates forceps with one shuttle in a first position and one shuttle in a second position.

FIG. 7B illustrates a shuttle 60 on the first working arm 30 being in a first position 60A and a shuttle 60 on the second working arm 32 being in a second position 60B. The bias device 80 on the shuttle 60 on the first working arm 30 cannot contact with second working arm 32 to create a bias device when the shuttles 60 are misaligned.

Figure 8:
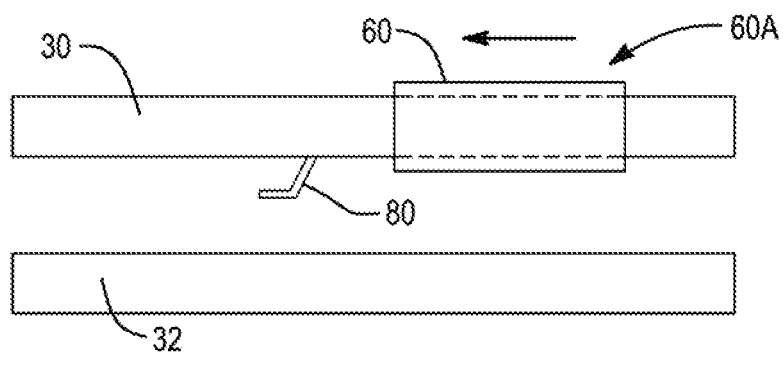
FIG. 8 illustrates forceps with a shuttle and bias device on the same working arm.

FIG. 8 illustrates both the bias device 80 and shuttle 60 being located on the first working arm 30 in a first position 60A. The shuttle 60 when moved in the direction as shown covers the bias device 80 to prevent a bias force from being created that moves the first working arm 30 relative to the second working arm 32. The second working arm 32 is free of a shuttle 60 and bias device 80.

Figure 9:
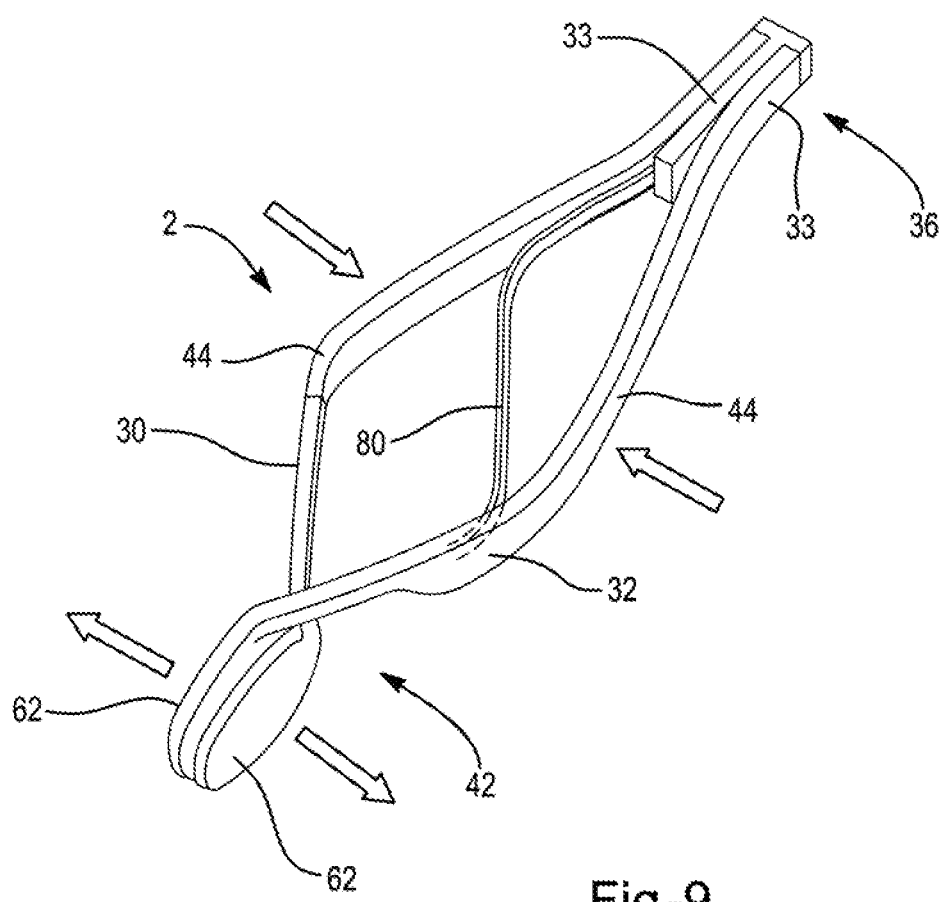
FIG. 9 illustrates a perspective view of forceps with distal ends that are bias closed.

FIG. 9 illustrates forceps 2 with a first working arm 30 and a second working arm 32 with a bias device 80 extending therebetween. The first end 30 and the second end 32 each include electrodes 33 and are connected at a pivot point 36. The first working arm 30 and the second working arm 32 include a gripping portion 44 and a cross-over 42 so that when a force, as indicated by the arrows, is applied to the first working arm 30 and the second working arm 32 the distal ends 62 move apart as indicated by the arrows.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

2 Forceps
10 Body
12 Inner shell
14 Deactivation feature
16 First activation button
18 Second activation button
20 Handle
30 First working arm 32 Second working arm
33 Electrode
37 Pivot
38 Electrical path
40 Distal end
42 Cross over
44 Gripping portion
60 Shuttle
60A First position
60B Second position
62 Distal end
64 Proximal end
66 Contact Zone
80 Bias device
82 Free end
84 Constrained end
86 Contact portion of spring
88 Breaks
100 Electrosurgical Device

We claim:

1. A device comprising:
a first working arm;
a second working arm;
a first shuttle located on the first working arm;
a second shuttle located on the second working arm; and
a bias device;
wherein the bias device contacts the second shuttle when the first shuttle is in a first position,
wherein the bias device biases the first working arm when the first shuttle is in the first position, and
wherein the bias device is free of biasing the first working arm when the first shuttle is in a second position.

2. The device of claim 1, wherein the bias device is located on the first shuttle.

3. The device of claim 1, wherein the bias device is free of contact with the second shuttle when the first shuttle is in the second position.

4. The device of claim 1, wherein the second shuttle on the second working arm is movable relative to the first shuttle on the first working arm.

5. The device of claim 1, wherein in the first position the first shuttle and the second shuttle are aligned.

6. The device of claim 5, wherein in the second position the first shuttle and the second shuttle are misaligned.

7. The device of claim 1, wherein the bias device comprises a spring.

8. The device of claim 1, wherein the bias device includes a constrained end coupled to the first shuttle and a free end that is configured to contact the second shuttle.

9. The device of claim 1, wherein the first shuttle and the second shuttle are longitudinally slidable relative to each other.

10. A device comprising:
a first working arm;
a second working arm;
a shuttle located on the first working arm;
a bias device located on the shuttle; and
a deactivation feature located on the second working arm;
wherein the bias device biases the first working arm away from the second working arm when the shuttle is misaligned with the deactivation feature, and wherein the bias device is free of biasing the first working arm when the shuttle is aligned with the deactivation feature.

11. The device of claim 10, wherein the deactivation feature comprises a recess in the second working arm.

12. The device of claim 10, wherein the bias device comprises a spring.

13. The device of claim 10, wherein the bias device includes a constrained end coupled to the shuttle and a free end that contacts the second working arm when the shuttle is misaligned with the deactivation feature.

14. A device comprising:
a first working arm;
a second working arm;
a first shuttle located on the first working arm;
a bias device located on the first shuttle; and
a second shuttle located on the second working arm;
wherein the bias device biases the first working arm when the first shuttle is aligned with the second shuttle, and wherein the bias device is free of biasing the first working arm when the first shuttle is misaligned with the second shuttle.

15. The device of claim 14, wherein the second shuttle on the second working arm is movable relative to the first shuttle on the first working arm.

16. The device of claim 14, wherein the bias device contacts the second shuttle when the first shuttle is aligned with the second shuttle.

17. The device of claim 16, wherein the bias device is free of contact with the second shuttle when the first shuttle and the second shuttle are misaligned.

18. The device of claim 14, wherein the bias device comprises a spring.

19. The device of claim 14, wherein the first shuttle and the second shuttle are longitudinally slidable relative to each other.

* * * * *